United States Patent [19]

Ueda et al.

[11] Patent Number: 5,495,744
[45] Date of Patent: Mar. 5, 1996

[54] METHOD OF CORRECTING COMPONENTIAL CONCENTRATION IN EXPIRATION AND EXPIRATION ANALYZER

[75] Inventors: Hideo Ueda, Osaka; Mitsuo Hiromoto, Kyoto; Meng Gang, Kyoto; Yutaka Yamasaki, Kyoto, all of Japan

[73] Assignee: Kyoto Dai-Ichi Kagaku Co., Ltd., Kyoto, Japan

[21] Appl. No.: 327,909

[22] Filed: Oct. 24, 1994

[30] Foreign Application Priority Data

Oct. 25, 1993 [JP] Japan ................. 5-290131

[51] Int. Cl.$^6$ ............ G01N 33/497; A61B 5/00; A61B 10/00
[52] U.S. Cl. ............ 73/1 G; 73/23.3; 128/719; 422/84; 436/900
[58] Field of Search ............ 73/1 G, 23.3; 128/719, 128/730; 422/84; 436/900

[56] References Cited

U.S. PATENT DOCUMENTS

| | | | |
|---|---|---|---|
| 3,830,630 | 8/1974 | Kiefer et al. | 422/84 |
| 3,834,375 | 9/1974 | Sanctuary et al. | 73/23.3 |
| 3,895,630 | 7/1975 | Bachman | 73/23.3 |
| 3,924,442 | 12/1975 | Kerho et al. | 73/1 G |
| 4,278,636 | 7/1981 | Voigt et al. | 128/719 |
| 4,809,810 | 3/1989 | Elfman et al. | 422/84 |
| 4,905,498 | 3/1990 | O'Donnell et al. | 73/23.3 |
| 5,270,009 | 12/1993 | Nakamori et al. | 73/1 G |
| 5,361,771 | 11/1994 | Craine et al. | 73/23.3 |
| 5,402,796 | 4/1995 | Packer et al. | 128/719 |

FOREIGN PATENT DOCUMENTS

| | | |
|---|---|---|
| 0467307A2 | 1/1992 | European Pat. Off. . |
| 2084321 | 4/1982 | United Kingdom ............ 128/719 |
| 2138949 | 10/1984 | United Kingdom ............ 73/1 G |
| WO83/00613 | 3/1983 | WIPO . |
| WO90/14043 | 11/1990 | WIPO . |
| WO91/03727 | 3/1991 | WIPO . |

OTHER PUBLICATIONS

Villarroel, "A Breath to Breath $CO_2$ Concentration Monitor with Flueric Sensor", 24th ACEMB, p. 250, 3 Nov. 1971.

*Primary Examiner*—Hezron E. Williams
*Assistant Examiner*—Daniel S. Larkin
*Attorney, Agent, or Firm*—Nikaido, Marmelstein, Murray & Oram

[57] ABSTRACT

A first sample measuring passage provided between a collection port and a suction pump has a sample gas measurer for measuring expiration components, while a second sample measuring passage which is provided in parallel with the first sample measuring passage has a standard gas measurer for measuring $O_2$ gas. Assuming that [A] represents a measured value of a target component in an expiration sample and $[b_1]$ represents $O_2$ concentration in the expiration sample, correction is made on the basis of:

$$[M]=f_1 \cdot (21-[a_1])[A]/(21-[b_1])$$

where [M] represents the corrected measured value of the target component, $[a_1]$ represents $O_2$ concentration in end-tidal air which is supplied as a constant such as 15.3, for example, and $f_1$ represents an experimentally prescribed coefficient such as 1.67, for example.

10 Claims, 2 Drawing Sheets

METHOD OF CORRECTING COMPONENTIAL CONCENTRATION IN EXPIRATION AND EXPIRATION ANALYZER

BACKGROUND OF THE INVENTION

1. Field of the Invention

The present invention relates to a method of correcting componential concentration, which is measured for analyzing expiration of a subject, with an analyzer such as a gas chromatograph, and an analyzer for implementing such a method.

2. Description of the Background Art

It has been recognized that expiration of a sick person also contains information about the persons, disease, and a study is now being made on analysis of such expiration in a clinical test which is made for diagnosing, curing or preventing the disease.

In expiration which is subjected to analysis, a part called end-tidal air is most suitably employed as a sample for the analyzer. The end-tidal air is the remaining part of the expiration from which an initial part containing air from a dead space is discarded. Since the end-tidal air contains only alveolar air with homogeneous concentration of expiration components, it is excellent as a specimen. In an expiration test, therefore, the end-tidal air is measured as the most reliable specimen expressing the state of the subject, while a specific apparatus is required for collecting the end-tidal air.

On the other hand, it may be impossible or difficult to test the end-tidal air, for some reason or other. For example, it is difficult to collect the end-tidal air from a subject such as a baby, a child, a soporose patient or an unconscious patient. If the subject is healthy but old, for example, it may also be difficult to test the end-tidal air in consideration of the subject's physical strength.

In order to readily collect expiration in a painless manner, a collecting mask or hood is applied to the subject for temporarily collecting the subject's expiration in a bag or directly guiding the same to an analyzer. However, the collecting mask, which can be prepared from that for supplying oxygen to a patient, cannot be brought into close contact with the subject in an airtight manner because the mask itself has holes for communicating with ambient air. When the expiration is collected through such a collecting mask, ambient air is inevitably mixed into the expiration. While it is also possible to collect the expiration by applying a mask or a hood to or covering the respiratory organ, ambient air is also inevitably mixed into the expiration since the respiratory organ cannot be sealed.

Thus, the expiration which is collected by a conventional method contains not only the alveolar air but air from the dead space and ambient air, unless the same is collected by a specific method.

SUMMARY OF THE INVENTION

A first object of the present invention is to provide a method of correctly calculating componential concentration of expiration also when an expiration sample collected from a subject contains air from a dead space and ambient air.

A second object of the present invention is to provide an expiration analyzer comprising such correction means.

The correction method according to the present invention has been proposed on the premise of such recognition that $O_2$ concentration and $CO_2$ concentration in end-tidal air are substantially constant regardless of the subject. Even if the expiration sample is diluted with ambient air and air exhaled from a dead space, $O_2$ concentration or $CO_2$ concentration in the expiration sample is measured as standard gas concentration, to obtain the dilution of the expiration sample from the measured value of the standard gas concentration with reference to $O_2$ concentration or $CO_2$ concentration in end-tidal air which is supplied as a constant, thereby correcting the measured value of the expiration componential concentration.

When $O_2$ gas is employed as standard gas, correction is made as follows:

$$[M]=f_1 \cdot (21-[a_1]) \, [A]/(21-[b_1]) \tag{1}$$

assuming that $[A]$ represents a target componential measured value of the expiration sample, $[b_1]$ represents $O_2$ concentration in the expiration sample, $[M]$ represents the corrected target componential measured value, $[a_1]$ represents $O_2$ concentration in end-tidal air which is supplied as a constant, and $f_1$ represents an experimentally prescribed coefficient.

When $CO_2$ gas is employed as standard gas, on the other hand, correction is made as follows:

$$[M]=f_2 \cdot [a_2][A]/[b_2] \tag{2}$$

assuming that $[b_2]$ represents $CO_2$ concentration in the expiration sample, $[a_2]$ represents $CO_2$ concentration in end-tidal air which is supplied as a constant, and $f_2$ represents an experimentally prescribed coefficient.

In order to implement this correction method, the expiration analyzer according to the present invention comprises a first sample measuring passage, provided with a sample gas measurer for measuring at least one or two components in expiration, for receiving an expiration sample of alveolar air which is mixed with at least one of air from a dead space and ambient air, a second sample measuring passage, provided with a standard gas measurer for measuring at least one of $O_2$ gas and $CO_2$ gas as standard gas, provided in parallel with the first sample measuring passage for receiving the same expiration sample as the first sample measuring passage, and a computing element for correcting a componential measured value in the expiration sample measured by the sample gas measurer through standard gas concentration in the expiration sample measured by the standard gas measurer with reference to concentration of the standard gas in end-tidal air. The computing element is implemented by a CPU(central processing unit).

In order to obtain the $O_2$ concentration reference value $[a_1]$ and the $CO_2$ concentration reference value $[a_2]$ of the standard gas, end-tidal air samples were collected from 28 normals and 26 patients.

Table 1 shows the results of $CO_2$ concentration values in expiration, which were measured with respect to the normals and the patients. Referring to Table 1, symbol n represents the numbers of the normals and the patients, symbol X represents mean $CO_2$ concentration values (vol. %), and symbol SD represents standard deviations of measured data distribution. The normals were 19 to 23 years of age and 21.1 years on the average, while the patients were 13 to 80 years of age and 52.7 years on the average.

TABLE 1

|  | Normal | Patient |
|---|---|---|
| n | 28 | 26 |
| x | 5.09 | 4.70 |
| SD | 0.48 | 0.45 |
| Average Age | 21.1 | 52.7 |
| Oldest | 23 | 80 |
| Youngest | 19 | 13 |

It is understood from Table 1 that the $CO_2$ concentration values in the end-tidal air are at similar levels with minimal individual differences between the normals and the patients (i.e. concentration values in the end-tidal air do not depend upon age or disease). Similar results were obtained also as to $O_2$ concentration values in the end-tidal air, with minimal individual differences between the normals and the patients.

Table 2 shows results of $O_2$ concentration values $[a_1]$ and $CO_2$ concentration values $[a_2]$ calculated from end-tidal air of 54 subjects including the normals and the patients. As understood from Table 2, the average concentration $[a_1]$ was 15.3 vol. %, the standard deviation SD was 0.64, the average $CO_2$ concentration $[a_2]$ was 4.9 vol. %, and the standard deviation SD was 0.51.

TABLE 2

|  | $O_2$ Concentration [a1] | $CO_2$ Concentration [a2] |
|---|---|---|
| Average Concentration | 15.3 (%) | 4.9 (%) |
| Standard Deviation (SD) | 0.64 | 0.51 |
| Number | 54 | 54 |

On the basis of the aforementioned results, the value 15.3 is employed as the $O_2$ concentration $[a_1]$ in end-tidal air in the equation (1), and the value 4.9 is employed as the $CO_2$ concentration $[a_2]$ in end-tidal air in the equation (2). $(21-[a_1])/(21-[b_1])$ in the equations (1) and $[a_2]/[b_2]$ in the equation (2) are coefficients for correcting dilution of expiration samples with ambient air and gas from dead spaces. Referring to the equation (1), the value "21" represents $O_2$ concentration (vol. %) in the air.

The concentration values $[a_1]$ and $[a_2]$, which may vary with, races and life styles of subjects, are preferably obtained for every control group.

While a gas bag for collecting expiration is prepared from a material causing neither adsorption nor decomposition of expiration componential gas and passages for feeding the expiration sample are heated to prevent the target component from reduction caused by condensation of moisture contained in the expiration, it has been discovered that the measured value is still reduced at a constant rate as compared with a value which is measured by directly introducing end-tidal air into a measurer. The values $f_1$ and $f_2$ appearing in the equations (1) and (2) respectively are adapted to correct the measured values reduced by the measuring method. In order to obtain the values $f_1$ and $f_2$, respiratory organ portions of subjects were covered with masks or hoods and expiration samples from the masks or hoods containing end-tidal air and remaining expiration with contamination of ambient air were measured directly or collected in gas bags having no gas adsorptivity for thereafter measuring expiration samples, while only end-tidal air samples were directly guided to an analyzer for measuring true components, so that the results were compared with each other. Table 3 shows the results.

TABLE 3

| Collection Method | Measured | | | Reference | Corrected Value | |
|---|---|---|---|---|---|---|
|  | [Ac] ppm | $CO_2$% | $O_2$% | ppm | [Ac']1 | [Ac']2 |
| 1. Hood Collection | 4.3 | 2.94 | 16.5 | 8.4 | 9.03 (108) | 9.1 (108) |
| 2. Hood Collection | 4.9 | 2.91 | 16.5 | 10.1 | 10.4 (103) | 10.4 (103) |
| 3. Mask Collection | 4.0 | 2.61 | 16.8 | 10.2 | 9.5 (93) | 9.1 (92) |
| 4. Mask Collection | 3.6 | 2.03 | 18.2 | 12.1 | 11.0 (91) | 12.2 (101) |
| 5. Hood Collection | 6.2 | 2.78 | 16.7 | 13.6 | 13.8 (101) | 13.7 (101) |

The measurement was made by three types of collecting methods, including that of covering the respiratory organ portions of the subjects with hoods for temporarily collecting the expiration samples in gas bags (Hood Collection; No.1, 2), that of covering the respiratory organ portions of the subjects with masks for temporarily collecting the expiration samples in gas bags (Mask Collection; No. 3, 4), and that of covering the respiratory organ portions of the subjects with hoods for directly incorporating the expiration samples in the analyzer (Hood Collection; No. 5), As to the measured values, [Ac] represents acetone concentration values (ppm) with respect to a target component of acetone. Further, "$CO_2$" represents $CO_2$ concentration values $[b_2]$ (vol. %) in the expiration samples, and "$O_2$" represents $O_2$ concentration values $[b_1]$ (vol. %) in the expiration samples. The reference values ("Reference") were obtained by directly measuring acetone concentration values in the end-tidal air by another device.

The corrected values [Ac']1 were obtained by prescribing a correction coefficient $f_1$ for correcting the five measured values [Ac] for most approaching the same to the reference values in the equation (1) with reference to $O_2$ gas serving as standard gas. At this time, the correction coefficient $f_1$ was obtained as 1.67.

Similarly, the corrected values [Ac']2 were obtained by prescribing a correction coefficient $f_2$ for correcting the five measured values [Ac] for most approaching the same to the reference values in the equation (2) with reference to $CO_2$ gas serving as standard gas. At this time, the correction coefficient $f_2$ was obtained as 1.26. Referring to Table 3, parenthesized numerals such as (108) and (93) show ratios to reference values of 100. From the results, the values 1.67 and 1.26 are set in a CPU(computing element) as the correction coefficients $f_1$ and $f_2$ in the equations (1) and (2) respectively. The coefficients $f_1$ and $f_2$, which vary with measured gas components and the structure of the apparatus, are preferably obtained for every apparatus specification.

According to the present invention, a measured value of target componential concentration is corrected with reference to $O_2$ concentration or $CO_2$ concentration in end-tidal air also in an expiration sample which is collected in a diluted state, whereby it is possible to correctly obtain target componential concentration also from an expiration sample of a subject whose end-tidal air is hard to test, in addition to an infant or an unconscious patient. While collection of only end-tidal air leads to a burden on the subject and requirement for a specific collecting apparatus, it is possible to correctly analyze expiration with neither burden nor specific apparatus according to the present invention.

DESCRIPTION OF THE PREFERRED EMBODIMENTS

Figure 1:
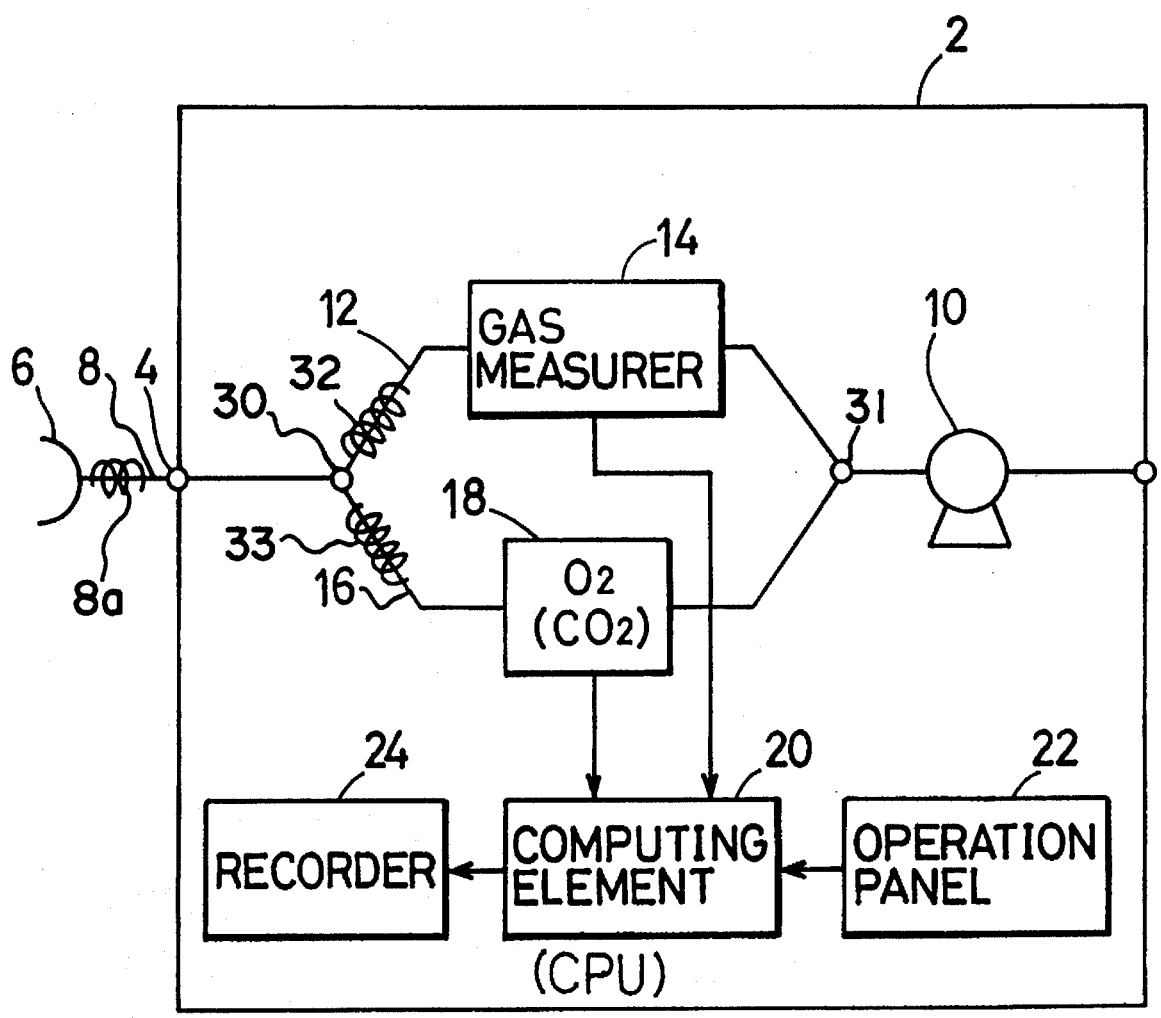
FIG. 1 is a block diagram showing an embodiment of the present invention.

FIG. 1 schematically illustrates an expiration analyzer 2 according to an embodiment of the present invention. The expiration analyzer 2 has a collection port 4, which is connected with a gas bag of a material having no gas absorptivity, so that an expiration sample of a subject collected in the gas bag is introduced into the analyzer 2 from the collection port 4. It is possible to connect the forward end of the collection port 4 with an expiration blowing part 8 having an appliance 6 to be applied to a respiratory organ or for covering the same, in order to directly collect expiration of the subject. The appliance 6 for covering the respiratory organ is prepared from a mask, a hood or a mouthpiece. A passage of the blowing part 8 is preferably formed by a heating pipe comprising a heater 8a wound on a tube, which is prepared from an elastic material such as polytetrafluoroethylene to cause neither adsorption nor reaction of gas contained in the expiration while facilitating handling. The heater is preferably temperature-controlled for heating the inner wall temperature of the tube to 40° to 50° C. so that moisture contained in the expiration is not condensed on the inner wall of the tube.

A suction pump 10 is provided for sucking the expiration from the gas bag or the expiration blowing part 8, while a sample gas measurer 14 is provided in a first sample measuring passage 12 connecting the collection port 4 with the suction pump 10. The sample gas measurer 14, which is a detector capable of measuring expiratory components, can include a gas treatment unit at need. The components measured by the sample gas measurer 14 are acetone, CO, $NH_3$, $CH_4$ and the like. The sample gas measurer 14 may be formed by a gas chromatograph. The flow rate of the suction pump 10 is preferably about 200 to 1000 ml/min.

A second sample measuring passage 16 having a standard gas measurer 18 is provided between the collection port 4 and the suction pump 10 in parallel with the first sample measuring passage 12. The standard gas measurer 18 is an $O_2$ or $CO_2$ measurer. The $O_2$ measurer, which may have any measurement principle, is of a system subjected to no interference with coexisting gas, and suitably formed by a magnetic or zirconia $O_2$ measurer. On the other hand, an NDIR (nondispersive infrared analyzer) type measurer is suitably employed as the $CO_2$ measurer for forming the standard gas measurer 18.

The first and second sample measuring passages 12 and 16 receive the expiration sample simultaneously, so that the gas measurers 14 and 18 can measure concentration values of the target components. When the collection port 4 is connected with a gas bag, measuring times in the sample measuring passages 12 and 16 may deviate from each other since the expiration sample is homogenized in the gas bag. Therefore, switching valves 30, 31 may be provided on confluent points located upstream and downstream in the sample measuring passages 12 and 16 respectively, for switching the expiration sample to be introduced into the sample measuring passages 12 and 16.

The passages between the collection port 4 and the gas measurers 14 and 18 are heated by heaters 32, 33 to about 40° to 50° C., to prevent condensation of the moisture contained in the expiration.

A CPU 20 receives detection signals from the gas measurers 14 and 18 respectively. An operation panel 22, which is provided with operation keys having functions of starting measurement and inputting an $O_2$ concentration reference value $[a_1]$, $CO_2$ concentration reference value $[a_2]$ and coefficients $f_1$ and $f_2$ for computing, is connected with the CPU 20. A recorder 24 records target componential concentration corrected by the CPU 20.

Figure 2A:
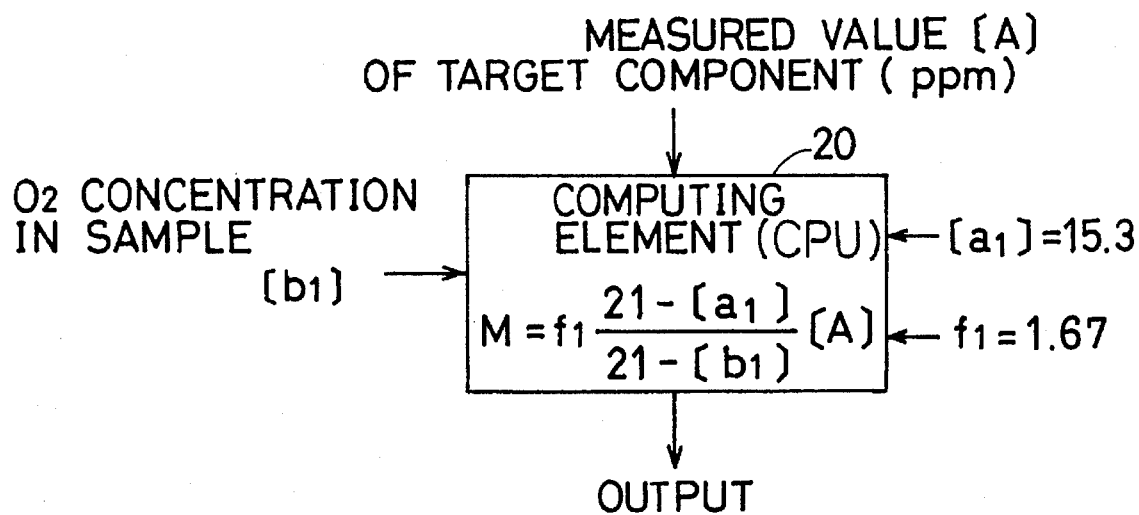
FIGS. 2A and 2B illustrate functions of a CPU in the embodiment shown in FIG. 1 with respect to standard gas measurers 18 which are formed by an $O_2$ measurer and a $CO_2$ measurer respectively.

When the standard gas measurer 18 is formed by an $O_2$ measurer, the CPU 20 functions as shown in FIG. 2A with the operational content expressed in the equation (1), to input the values 15.3 and 1.67 as the $O_2$ concentration reference value $[a_1]$ and the coefficient $f_1$ respectively from the operation panel 22. The CPU 20 further incorporates the actually measured value [A] of the target component and the $O_2$ concentration (vol. %) from the sample and standard gas measurers 14 and 18 respectively to carry out correction operation, and outputs the result to the recorder 24.

Figure 2B:
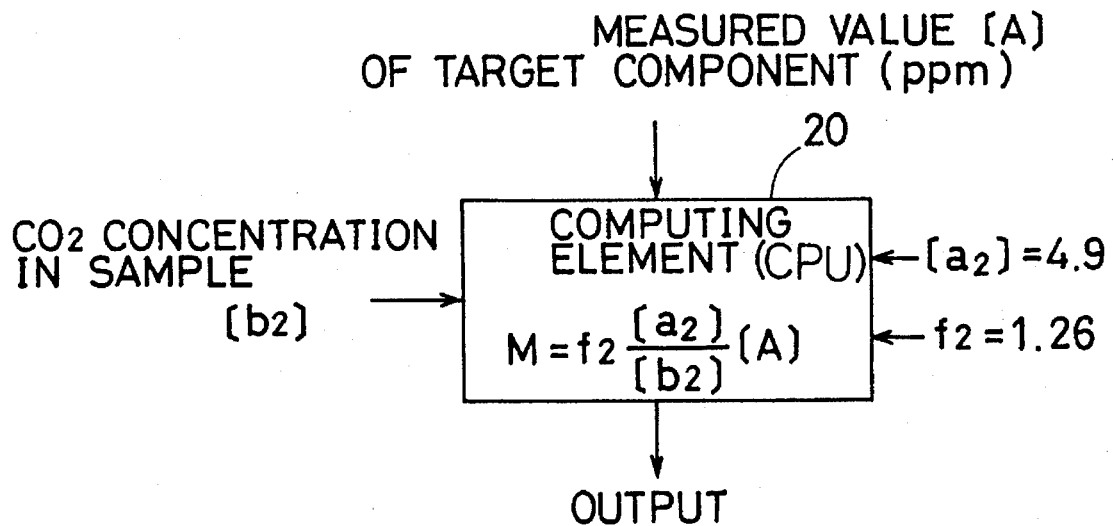

When the standard gas measurer 18 is formed by a $CO_2$ measurer, on the other hand, the CPU 20 functions as shown in FIG. 2B with the operational content expressed in the equation (2), to input the values 4.9 and 1.26 as the $CO_2$ concentration reference value $[a_2]$ and the coefficient $f_2$ respectively from the operation panel 22. The CPU 20 further incorporates the actually measured value [A] of the target component and the $CO_2$ concentration (vol. %) from the sample and standard gas measurers 14 and 18 respectively to carry out correction operation, and outputs the result to the recorder 24.

When the standard gas measurer 18 can measure both $O_2$ and $CO_2$, it is possible to more correctly carry out the correction operation for calculating average values of correction results through both of the equations (1) and (2), for example.

While the standard gas measurer 18 is independent of the sample gas measurer 14 in the embodiment shown in FIG. 1, the standard gas measurer 18 can be omitted if the sample gas measurer 14 can measure a plurality of components including $O_2$ or $CO_2$. In this case, the sample measuring passage 16 can also be omitted, to simplify the structure.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. A method of correcting componential concentration in expiration, comprising the steps of:

analyzing an expiration sample of alveolar air, being mixed with at least one of air from a dead space and ambient air, for obtaining a measured value of a target component;

measuring at least one of $O_2$ gas concentration and $CO_2$ gas concentration as a standard gas concentration in said expiration sample; and correcting said measured value of said target component by a measured value of said standard gas concentration in said expiration sample with reference to a standard gas concentration in end-tidal air.

2. A method of correcting componential concentration in expiration in accordance with claim 1, wherein said steps of obtaining said measured value of said target component and measuring said standard gas concentration are carried out by measuring means being different from each other.

3. A method of correcting componential concentration in expiration in accordance with claim 1, wherein said steps of obtaining said measured value of said target component and measuring said standard gas concentration are simultaneously carried out by the same measuring means.

4. A method of correcting componential concentration in expiration in accordance with claim 1, wherein said correction is made on the basis of:

$$[M] = f_1 \cdot (21 - [a_1]) [A]/(21 - [b_1])$$

assuming that [A] represents said measured value of said target component in said expiration sample, $[b_1]$ represents said $O_2$ concentration in said expiration sample, [M] represents corrected said measured value of said target component, $[a_1]$ represents $O_2$ concentration in end-tidal air, being a constant, and $f_1$ represents an experimentally prescribed coefficient.

5. A method of correcting componential concentration in expiration in accordance with claim 1, wherein said correction is made on the basis of:

$$[M] = f_2 \cdot [a_2][A]/[b_2]$$

assuming that [A] represents said measured value of said target component in said expiration sample, $[b_2]$ represents said $CO_2$ concentration in said expiration sample, [M] represents corrected said measured value of said target component, $[a_2]$ represents $CO_2$ concentration in end-tidal air, being a constant, and $f_2$ represents an experimentally prescribed coefficient.

6. An expiration analyzer comprising:

a first sample measuring passage means, having a sample gas measurer which measures at least one or two components in expiration, for receiving from a collection port an expiration sample of alveolar air being mixed with at least one of air from a dead space and ambient air;

a second sample measuring passage means, having a standard gas measurer which measures at least one of $O_2$ gas and $CO_2$ gas as standard gas and being provided in parallel with said first sample measuring passage means, for receiving from said collection port said expiration sample being identical to that guided in said first sample measuring passage means;

a heating means for heating passages between said collection port and said sample and standard gas measurers; and a computing means for correcting a componential measured value in said expiration sample, being measured by said sample gas measurer, by a measured value of said standard gas concentration in said expiration sample, being measured by said standard gas measurer, with reference to concentration of a standard gas in end-tidal air.

7. An expiration analyzer in accordance with claim 6, further comprising a suction pump for sucking the expiration sample into said first and second sample measuring passages through said collection port.

8. An expiration analyzer in accordance with claim 6, further comprising a switching valve being provided on a confluent point located upstream in said first and second sample measuring passages, for switching the expiration sample to be introduced into said first and second sample measuring passages.

9. An expiration analyzer in accordance with claim 6, wherein said computing element makes said correction on the basis of:

$$[M] = f_1 \cdot (21 - [a_1]) [A]/(21 - [b_1])$$

assuming that [A] represents said measured value of said target component in said expiration sample, $[b_1]$ represents said $O_2$ concentration in said expiration sample, [M] represents corrected said measured value of said target component, $[a_1]$ represents $O_2$ concentration in end-tidal air, being a constant, and $f_1$ represents an experimentally presecribed coefficient.

10. An expiration analyzer in accordance with claim 6, wherein said computing element makes said correction on the basis of:

$$[M] = f_2 \cdot [a_2][A]/[b_2]$$

assuming that [A] represents said measured value of said target component in said expiration sample, $[b_2]$ represents said $CO_2$ concentration in said expiration sample, [M] represents corrected said measured value of said target component, $[a_2]$ represents $CO_2$ concentration in end-tidal air, being a constrant, and $f_2$ represents an experimentally prescribed coefficient.

* * * * *